(12) United States Patent
Hortobágyi et al.

(10) Patent No.: US 10,759,734 B2
(45) Date of Patent: Sep. 1, 2020

(54) PROCESS FOR THE PREPARATION AND PURIFICATION OF MISOPROSTOL

(71) Applicant: CHINOIN PHARMACEUTICAL AND CHEMICAL WORKS PRIVATE CO. LTD., Budapest (HU)

(72) Inventors: Irén Hortobágyi, Budapest (HU); István Lászlófi, Nagykálló (HU); Zsuzsanna Kardos, Budapest (HU); József Molnár, Biatorbágy (HU); László Takács, Budapest (HU); Kornélia Horváth, Budapest (HU)

(73) Assignee: CHINOIN PHARMACEUTICAL AND CHEMICAL WORKS PRIVATE COMPANY LTD., Budapest (HU)

(*) Notice: Subject to any disclaimer, the term of this patent is extended or adjusted under 35 U.S.C. 154(b) by 0 days.

(21) Appl. No.: 16/630,125

(22) PCT Filed: Jun. 29, 2018

(86) PCT No.: PCT/EP2018/067560
§ 371 (c)(1),
(2) Date: Jan. 10, 2020

(87) PCT Pub. No.: WO2019/011668
PCT Pub. Date: Jan. 17, 2019

(65) Prior Publication Data
US 2020/0165186 A1  May 28, 2020

(30) Foreign Application Priority Data
Jul. 11, 2017  (HU) .................................. 1700308

(51) Int. Cl.
*C07C 69/738* (2006.01)
*C07F 7/22* (2006.01)
(Continued)

(52) U.S. Cl.
CPC ............ *C07C 69/738* (2013.01); *C07C 45/00* (2013.01); *C07F 1/08* (2013.01); *C07F 7/2208* (2013.01)

(58) Field of Classification Search
CPC ..... C07C 69/378; C07C 45/00; C07F 7/2208; C07F 1/08
See application file for complete search history.

(56) References Cited

U.S. PATENT DOCUMENTS 4,904,820 A  2/1990 Campbell et al.
5,684,177 A  11/1997 Lu et al.
(Continued)

FOREIGN PATENT DOCUMENTS

WO  WO 96/28419 A1  9/1996

OTHER PUBLICATIONS

International Search Report (PCT/ISA/210) issued in PCT/EP2018/067560, dated Sep. 12, 2018.
(Continued)

*Primary Examiner* — Jafar F Parsa
(74) *Attorney, Agent, or Firm* — Birch, Stewart, Kolasch & Birch, LLP

(57) ABSTRACT

A process of preparing compounds of general formula I,

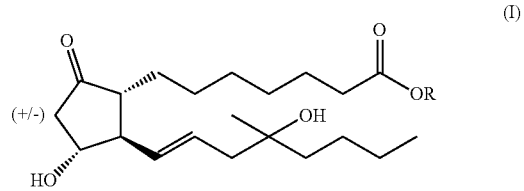

by cuprate coupling of a vinyl cuprate of general formula II

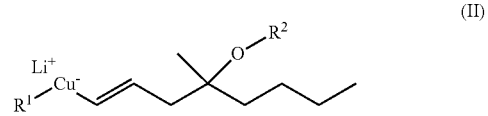

with a protected enone of general formula IV

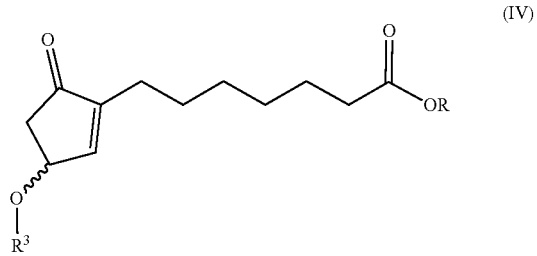

to produce a compound of general formula (V)

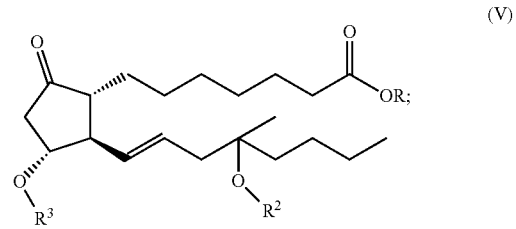

(Continued)

removing the protecting groups of the compound of general formula (V) and purifying the compound of general formula (I) by chromatography; wherein the vinyl cuprate of formula (II) is prepared by reacting a vinyl stannane of formula III with copper halide CuX and alkyllithium R1Li

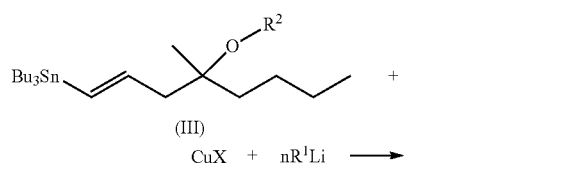

and wherein an excess of the alkyllithium is decomposed before the said coupling reaction.

18 Claims, No Drawings

(51) Int. Cl.
*C07F 1/08* (2006.01)
*C07C 45/00* (2006.01)

(56) References Cited

U.S. PATENT DOCUMENTS 6,013,823 A  1/2000 Mamarella et al.
2010/0324313 A1  12/2010 Hogan et al.

OTHER PUBLICATIONS

Written Opinion (PCT/ISA/237) issued in PCT/EP2018/067560, dated Sep. 12, 2018.
Behling et al., "In situ Cuprate Formation via Transmetalation between Vinylstannanes and Higher Order Cyanocuprates", J. Am. Chem. Soc., vol. 110, 1988, 2641-2643.
Roston et al. "Two-dimensional liquid chromatographic method for resolution of prostaglandin enantiomers", Analytical Chemistry, vol. 60, No. 9, May 1, 1988, pp. 948-950.

PROCESS FOR THE PREPARATION AND PURIFICATION OF MISOPROSTOL

The subject of the invention is process for the preparation of the compounds of general formula I,

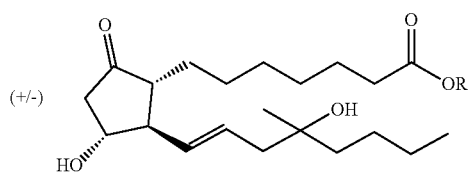

where R represents a straight- or branched-chain $C_{1-4}$ alkyl group.

Misoprostol (Ia) (R=methyl), a synthetic, modified PGE1 derivative, falling under general formula I, is a racemic compound, a mixture of 4 stereoisomers.

The following structural formula of the racemic compound indicates relative stereochemistry.

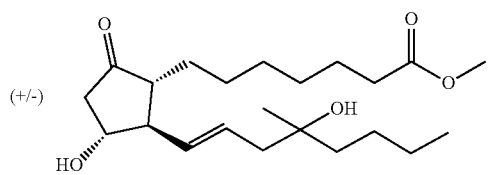

Racemic misoprostol is a 1:1:1:1 ratio mixture of 4 isomers.

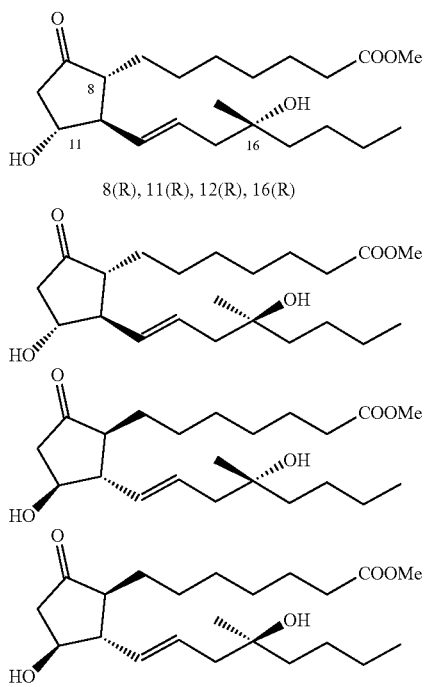

Therapeutic use of misoprostol is to reduce the risk to develop gastric and duodenal ulcer induced by nonsteroidal anti-inflammatories (NSAIDs). drugs.com/pro/misoprostol, down-load 18 Feb. 2016). Owing to this protective effect, it is also applied together with nonsteroidal anti-inflammatories, in combination preparations (drugs.com/cdi/diclofenac-misoprostol, down-load 18 Feb. 2016). Misoprostol in itself is also capable to induce labor (ferring.com/en/media/press-release/2013/misodel-17oct13/, download 18 Feb. 2016).

For the preparation of misoprostol several methods are known.

In the process described in patent specification CA 1040197 A misoprostol was synthetized in a two-component cuprate coupling.

The unprotected or THP-group-protected (THP=tetrahydropyranyl-) cyclopentenone ester was reacted with a so-called "Lower Order" cuprate reagent (Scheme 1).

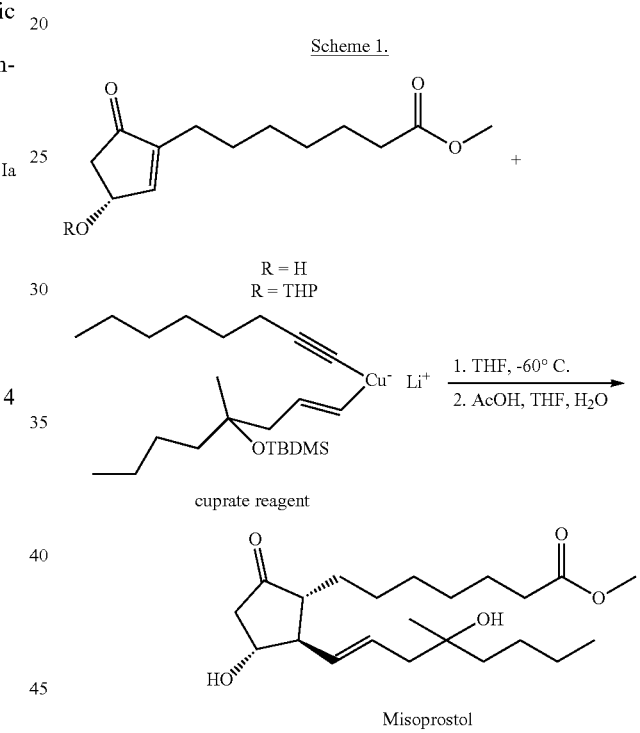

The cuprate reagent was prepared from TBDMS-octynol (TBDMS=tert-butyldimethylsilyl-) (Scheme 2).

The triple bond was reduced with catecholborane or with diisobutylaluminum hydride, the substituent incorporating the boron or the aluminum atom was then exchanged for iodine.

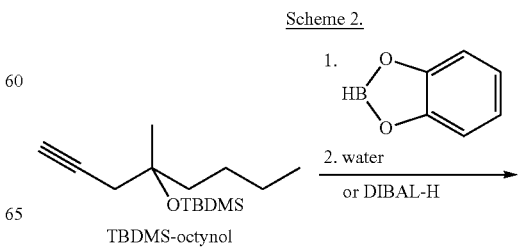

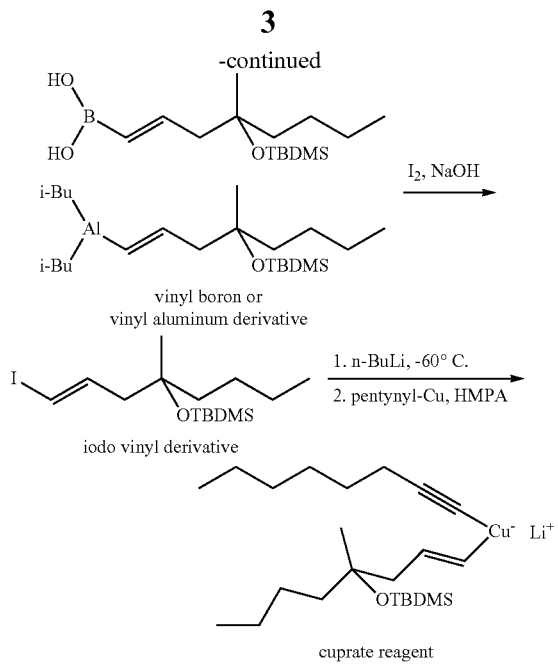

The vinyl lithium component—obtained from the iodo compound—was reacted with the solution of pentynyl-copper in hexamethylphosphoramide (HMPA) at −60° C. to result the copper compound suitable for the cuprate coupling.

The advantage of the method is that the cuprate coupling was successfully applied for the preparation of misoprostol, however, the synthesis also has several disadvantages:
  reduction of the octynol with catecholborane or with diisobutylaluminum hydride proceeds in very poor yield
  during the reaction, beside the expected trans-olefin, the product with cis geometry is also formed
  preparation of the cuprate reagent requires cooling to −60° C. and the use of carcinogenic HMPA.

The method described in patent specification U.S. Pat. No. 4,904,820 is a developed version of the cuprate coupling. The TES-protected (TES=triethylsilyl-) cyclopentenone derivative was reacted with a "Higher Order" cuprate reagent (X=CN, SCN, OSO$_2$CF$_3$, S-phenyl). The synthesis of the cuprate reagent was significantly simplified (Scheme 3).

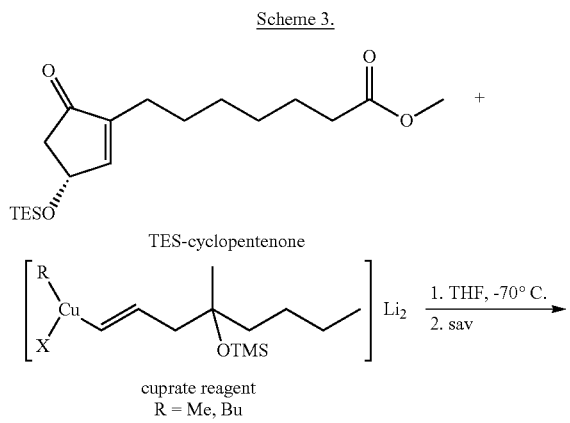

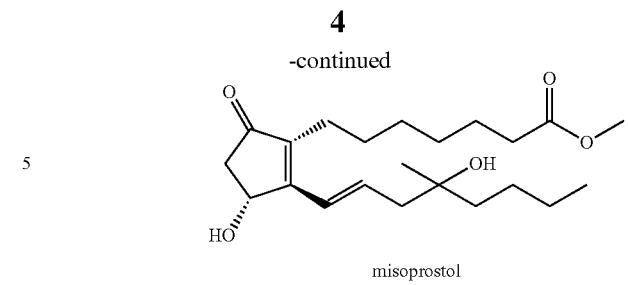

To obtain the cuprate reagent copper(I)cyanide was treated with Me- or Bu-lithium. Reaction of the thus obtained copper compound with another alkyllithium gave the dialkyl cuprate, which on reaction with vinyl stannane resulted the vinyl cuprate required for the coupling (Scheme 4).

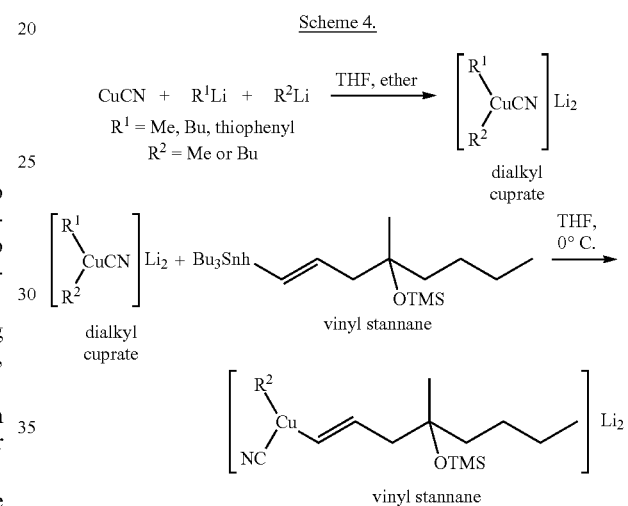

Advantages of the Method:
  preparation of the vinyl stannane is more simple than that of the iodo vinyl derivative
  reaction of the "Higher-Order" cuprate with vinyl stannane does not require deep-freezing.
Disadvantages of the Method:
  it uses poisonous CuCN reagent
  the vinyl stannane is prepared by reduction of TMS-octynol (TMS=trimethylsilyl-) with tributyltinhydride. During the reduction 15% of cis-isomer impurity is formed (Scheme 5).

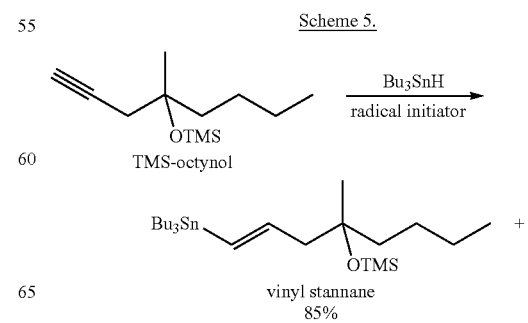

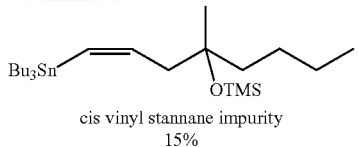

cis vinyl stannane impurity
15%

U.S. Pat. No. 5,055,604 describes further development, the reduction of TMS-octynol was namely carried out with zirconocene chloride hydride (Scheme 6).

Scheme 6.

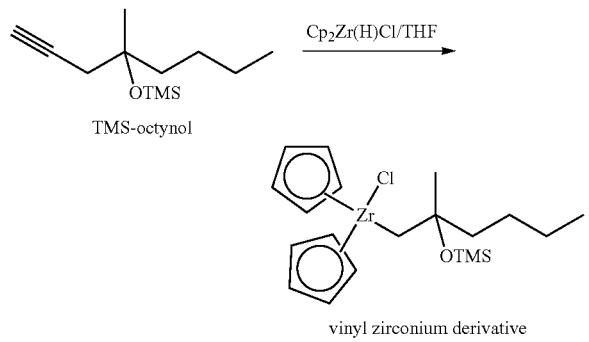

From the resulting vinyl zirconium derivative the "Higher Order" cuprate reagent was prepared and reacted with TES-cyclopentenone. After acidic hydrolysis of the TES-group, misoprostol was obtained.

Advantage of the Method:
the vinyl zirconium derivative is not contaminated with the cis isomer.

Disadvantage of the Method:
zirconocene chloride hydride is an expensive reagent.

In the method described in patent specification U.S. Pat. No. 5,684,177 the vinyl cuprate reagent for the conjugated addition reaction was obtained by first reacting the alkyllithium with copper halide, then treating the obtained "Lower Order" dialkyl cuprate with vinyl stannane (Scheme 7).

Scheme 7.

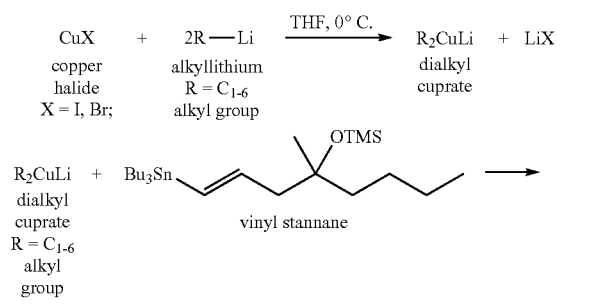

Studying the process it was found that using more than 2 equivalents of alkyllithium for the preparation of the dialkyl cuprate, the reaction of the "Lower Order" cuprate with the vinyl stannane may be performed at 0- −30° C., and cooling to −(−78)° C to obtain the vinyl cuprate is not necessary.

If the amount of the alkyllithium is 2 equivalents or less, the vinyl cuprate is not formed.

If the amount of the alkyllithium is too high, undesired by-products increases.

As described in the claims of the patent, the ratio of the alkyllithium is 2.05-4 mols for 1 mol of copper halide.

Favorable molar ratios are: alkyllithium:copper halide=2.1-2.25:1.

The effect of the addition order was also investigated. The orders copper halide-alkyllithium-vinyl stannane or vinyl stannane-copper halide-alkyllithium were equally applicable to obtain the vinyl cuprate reagent.

Advantages of the Method:
by using more than 2 equivalents of alkyllithium the vinyl cuprate reagent may be prepared at to 0 to −30° C. and deep-freezing to −78° C. is not necessary.
the use of the poisonous CuCN is avoided.

Disadvantages of the Method:
the alkyllithium excess causes the formation of undesired by-products (e.g. instead of 1,4-addition 1,2-addition takes place)
because of the formation of by-products the yield is lower.

In the method described in patent specification EP 0943607 the unprotected octynol was reacted with tributyltin hydride.

The unprotected cis- and trans-HO-vinyl stannane isomers may namely be separated by column chromatography, thus the cuprate reagent used in the coupling reaction will not contain cis-isomer contamination (Scheme 8).

Scheme 8.

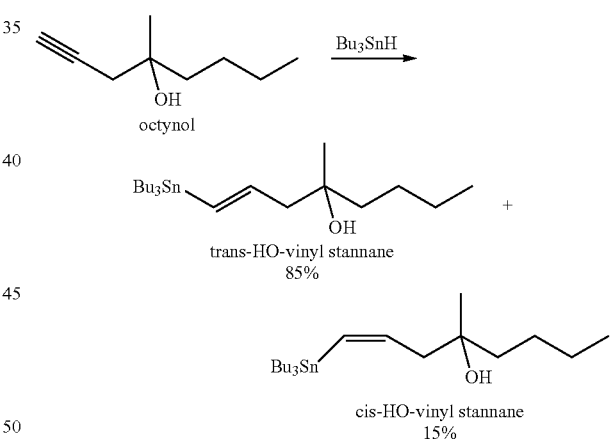

The trans-HO-vinyl stannane was then transformed into the required vinyl cuprate reagent in the presence of copper salt (CuY), alkyllithium (RLi), Lewis acid (G) and lithium salt (Z) of various molar ratios (Scheme 9).

Addition order of the reagents was also varied and investigated when preparing the vinyl cuprate.

Scheme 9.

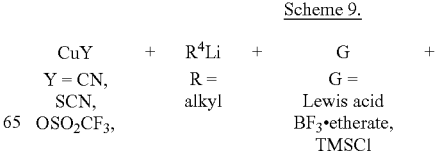

-continued

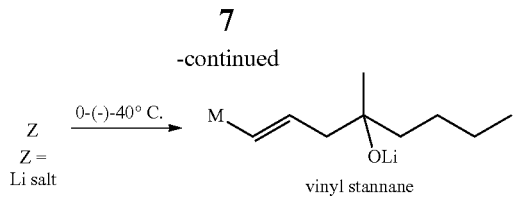

vinyl stannane

| Molar ratios of the reagents | | | | |
|---|---|---|---|---|
| CuY | R⁴Li | G | Z | M |
| 1 | 3 | — | — | Li₂(Y)Cu—R⁴ |
| 1 | 4 | — | — | Li₂(Y)Cu—CH=CH—C(CH₃)(OLi)—propyl |
| 1 | 2 | 1 | — | G•Li(Y)Cu— |
| 1 | 3 | 1 | — | G•Li₂(Y)Cu—R⁴ |
| 1 | 4 | 1 | — | G·Li₂(Y)Cu—CH=CH—C(CH₃)(OLi)—propyl |
| 1 | 2 | 1 | 1 | G—Liz•Li(Y)Cu— |

The yield of the cuprate coupling reaction was the highest if the CuY:RLi ratio was 1:3 or 1:4.

Additives (Lewis acids, lithium salts) did not improve the yield of the cuprate coupling.

The addition order of the reagents did not really influence the reaction.

Advantages of the Method:
  simple method to remove the cis stannane impurity
  the cuprate reagent is prepared at to 0 to –b 40° C., deep-freezing is not needed.

Disadvantage of the Method:
  use of the poisonous copper cyanide.

Patent specification WO 2016005943 A1 describes the preparation of prostaglandins by two-component coupling. According to the method the protected cyclopentenone is reacted with the vinyl boron derivative in the presence of rhodium-containing [RhC(1,5-cyclooctadiene)]₂ catalyst (Scheme 10).

Scheme 10.

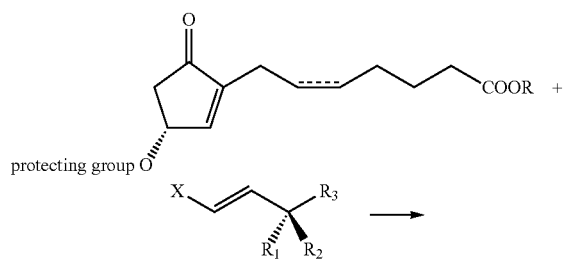

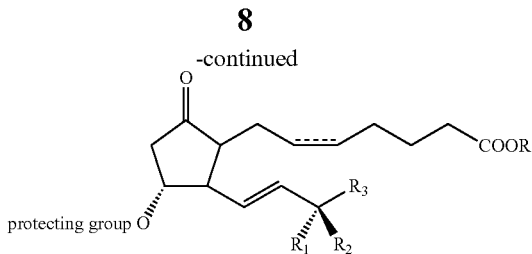

Advantages of the Method:
  no reaction under deep-freezing is required
  no poisonous organic copper or tin compound or expensive and chemically sensitive organic zirconium compound is used
  no poisonous cyanide ligand is used.

Disadvantages of the Method:
  the coupling has to be carried out in microwave reactor which hinders scale-up
  under thermic conditions the coupling reaction requires several days to take place.

The subject of our invention is preparation of the compound of general formula I

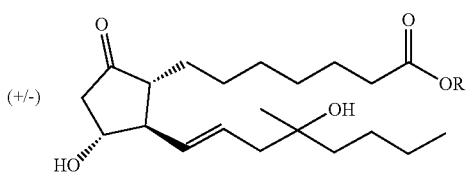

where R stands for straight- or branched-chain $C_{1-4}$ alkyl group
by cuprate coupling of the vinyl cuprate of general formula II
prepared by reacting the vinyl stannane of the general formula III with copper halide CuX and alkyllithium $R^1Li$

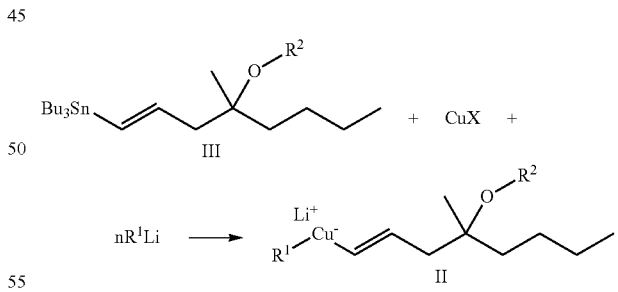

wherein:
$R^2$ stands for H or an alcohol-protecting group which may contain silicium atom, as for instance trimethylsilyl, triethylsilyl, tert.-butyldimethylsilyl group, or a cyclic or open-chain alkyl group containing oxygen atom, as for instance tetrahydropyranyl, methoxymethyl or ethoxymethyl group;
X means I, Br, CN, SCN, $OSO_2CF_3$
$R^1$ represents $C_{1-6}$ alkyl group
n>2, if $R^2$ is not hydrogen atom, n>3, if $R^2$ is hydrogen atom;

and the protected enone of the general formula IV

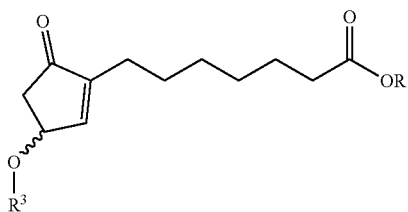

where R³ represents THP- or trialkylsilyl-group and the meaning of R is as defined above takes part in the cuprate reaction
characterized by that
  a.) the excess of the alkyllithium, which is applied as compared to the Cu(I)iodide
    in the case of R²≠H in 2-2.4 molar ratio,
    in the case of R²=H in 3-3.4 molar ratio,
    is decomposed before the coupling reaction of II and IV,
  b.) protecting groups of the resulting compound of general formula V

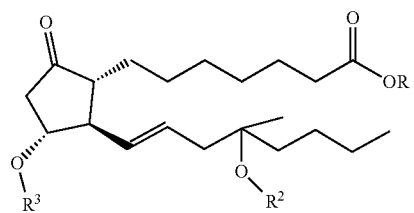

where the meanings of R, R² and R³ are as defined above,
  are removed, the obtained compound of the general formula I is purified by chromatography.

To prepare misoprostol, compound I according to the invention where R stands for methyl group, the reagent needed for the cuprate coupling is prepared by the reaction of vinyl stannane (85:15 ratio mixture of the trans and cis isomers) with copper iodide and methyllithium.

U.S. Pat. No. 5,684,177 studies in detail the molar ratios of alkyllithium compared to copper(I)halide in the cuprate reagent preparation. As given in the claims, the amount of the alkyllithium is 2.05-4 mol for 1 mol of copper(I)halide. Favorable alkyllithium-copper(I)halide ratios are 2.1-2.25:1.

According to our experiments, to obtain the vinyl cuprate reagent in acceptable yield, the MeLi/CuI molar ratio should be higher than 2. In our case (R²≠H) a 2.4-fold excess proved to be the most favorable.

The excess of the methyllithium, however, causes by-products formation, which decreases the yield and renders purification of the product more difficult.

The novelty of our invention is that after the formation of the cuprate reagent, but before the cuprate coupling, the methyllithium excess is decomposed in "one-pot" method.

In our process, on the effect of the methyllithium excess, the vinyl cuprate reagent is formed in sufficiently high conversion and since the excess of the methyllithium is decomposed after the cuprate reagent formation, the amount of the impurities coming from the coupling reaction is significantly diminished.

Decomposition of the methyllithium excess may be effected with any kind of compound which in non-aqueous medium reacts with the methyllithium, but neither itself, nor its derivative given with methyllithium reacts with the starting materials or the product of the cuprate conjugated addition.

Reagents suitable to decompose the methyllithium excess are ketones, esters and halogenated silylating agents.

Most suitable reagents to decompose the excess of methyllithium are small molar weight ketones, esters or halogenated silylating agents, as their excess and the compounds arising from them in the methyllithium reaction are easily removed from the reaction mixture, for instance by evaporation or by chromatographic purification.

The most suitable reagents to decompose the excess of methyllithium are acetone, ethyl acetate or trimethylsilyl chloride.

After the acidic decomposition the reaction of methyllithium with acetone results tertiary-butanol, that with ethyl acetate gives acetone or acetone and tertiary-butanol, with trimethylsilyl chloride results tetramethylsilane. Each of these compounds has low boiling point and may be removed from the reaction mixture by simple evaporation.

Following decomposition of the methyllithium excess, the vinyl cuprate reagent is reacted in one-pot reaction with the TMS-enone at −55° C., in tetrahydrofuran.

The reaction mixture obtained after decomposition and work-up contains the protected TMS-misoprostol crude product.

Removal of the protecting groups in methanol with pyridinium tosylate gives the crude misoprostol.

Misoprostol is an oil, to meet the quality required by USP and PhEur specifications it has to be purified by column chromatography.

| Name | Impurity Structural formula | Requirements by USP and PhEur [HPLC m%] |
|---|---|---|
| misoprostol A | (+/−) | ≤0.10 |

| | Impurity | Requirements by USP and PhEur |
|---|---|---|
| Name | Structural formula | [HPLC m%] |
| 8-iso-misoprostol | [structural formula] | ≤0.3 |
| 12-iso-misoprostol | [structural formula] | ≤1.0 |
| Other impurities, individually | — | ≤0.10 |
| Related impurities, total | — | ≤1.5 |

For column chromatographic purification, gravity chromatography was chosen.

Gravity chromatography is more advantageous than high-pressure preparative or medium-pressure "flash" chromatography, since
- it is cost-saving and easy to realize industrially
- it does not require expensive pressure-proof equipment
- the silica gel used for the stationary phase is cheaper than those used in the medium- and high-pressure chromatographic systems
- on the column used in the gravity chromatography purification is performed in one run which shortens the production time.

In the purification process as stationary phase we applied the most widely used and most economical irregular Kieselgel Si 60 (0.063-0.200 mm) (maker: Merck), the significantly more expensive spherical YMC S75, YMC S150 (maker: YMC Co. Ltd.), Chromatorex MB 70-40/75, Chromatorex MB70-75/200 (maker: Fuji Silysia Chen. Ltd) and the irregular Sepra Silica 50 (Fenomenex Ltd) silica gels.

As for eluent we used multicomponent mixtures. As for polar component of the multicomponent system we applied ketone-, ether-, ester- and alcohol-type solvents, while for apolar component we used hydrocarbon, aromatic hydrocarbon, halogenated hydrocarbon and ether-type solvents.

Thus, stepwise gradient mixtures of solvents
hexane:ethyl acetate,
toluene:ethyl acetate, toluene:tetrahydrofuran
dichloromethane:acetone, dichloromethane:methyl ethyl ketone, dichloromethane:tetrahydrofuran
diisopropyl ether:acetone, diisopropyl ether:methyl ethyl ketone, diisopropyl ether:isopropanol
diisopropyl ether:acetone:methanol
were applied.

During our chromatographic experiments we found that the best purification may be reached by using solvent mixtures which contain alcohol. However, the amount of one impurity, 8-iso-misoprostol, significantly increased, instead of decreasing, during the chromatographic purification, rendering the use of this method questionable.

Solution to the problem was brought by our innovative finding of adding 0.1-0.01%, preferably 0.05% of acetic acid or formic acid to the eluent of the chromatography. Acidity of the eluent blocked the basic sites of the silica gel of amphoteric character hindering thus the degradation of the chemically sensitive misoprostol into 8-iso-misoprostol which takes place on the effect of base.

The favorable effect of the acid does not appear below an acid content of 0.01%, while an acid content higher than 0.1% may cause the formation of misoprostol-A and 8-iso-misoprostol impurities.

To hinder the formation of 8-iso-misoprostol impurity, both acetic and formic acid are suitable, however, because of easier removal the use formic acid is more advantageous.

Misoprostol product meeting the quality according to the present specification was obtained in best yield by using YMC S75 silica gel and as eluent, diisopropyl ether:isopropanol gradient mixtures, containing 0.05% of formic acid.

Applying the much cheaper Kieselgel Si 60 (0.063-0.200 mm) silica gel the amount of the impurities eluting before misoprostol decreased to the value allowed by specification, but the amount of the related impurities eluting at RRT>1 remained higher than the allowed 0.10 mass %.

If, however, the concentrated main fraction of the purification chromatography was clarified by filtration through active carbon, we found in surprise that the hardly removable related impurities more polar than misoprostol, bonded on the surface of the active carbon in such an extent that their amount decreased to below the allowed limit of 0.10 mass %.

Thus, misoprostol of appropriate quality may be prepared not only by chromatography on the expensive spherical YMC S75 silica gel using diisopropyl ether:isopropanol 0.05% formic acid mixtures as eluent, but also by chromatography on the much cheaper irregular Kieselgel Si 60 (0.063-0.200 mm) silica gel using diisopropyl ether:isopropanol 0.05% formic acid or diisopropyl ether:acetone:methanol 0.05% formic acid mixtures as eluent, followed by filtration on active carbon.

The last step of the purification process of misoprostol is filtration through silica gel, in order to remove the contaminations arising from the solvents used during the purifications.

Filtration through silica gel was performed on Kieselgel Si 60 (0.063-0.200 mm) silica gel, using stepwise gradient mixtures of distilled dichloromethane:acetone 0.05% formic acid and methyl tert.-butyl ether:acetone and 0.05% formic acid solvents.

The fractions containing the product were united, washed with sodium hydrogen carbonate solution and with water, clarified, dried, filtered and evaporated.

Applying the above method according to the invention misoprostol product of appropriate quality meeting the present specification may be prepared.

Here below we demonstrate the characteristics of some of the stationary phases applied in the above purification process:

Fuji Silysia Chemical Ltd.

| CHROMATOREX MB 70-40/75 | | | |
|---|---|---|---|
| Item | Unit | Specifications | Lot Data |
| Surface Area | m²/g | 450-550 | 483 |
| Pore Volume | ml/g | 0.70-0.90 | 0.85 |
| Bulk Density | g/ml | 0.40-0.60 | 0.53 |
| pH | — | 6.0-8.0 | 7.5 |
| Loss on Drying | % | 3.0-7.0 | 5.6 |
| ParticleSize Distribution | | | |
| on 75 µm | % | 10.0% max. | 1.4 |
| 38-75 µm | % | 80.0% min. | 94.0 |
| thru 38 µm | % | 10.0% max. | 4.6 |

| CHROMATOREX MB 70-75/200 | | | |
|---|---|---|---|
| Item | Unit | Specifications | Lot Data |
| Surface Area | m²/g | 450-550 | 503 |
| Pore Volume | ml/g | 0.70-0.90 | 0.87 |
| Bulk Density | g/ml | 0.40-0.60 | 0.51 |
| pH | — | 6.0-8.0 | 7.2 |
| Loss on Drying | % | 3.0-7.0 | 4.7 |
| Particle Size Distribution | | | |
| on 180 µm | % | 10.0% max. | 0.0 |
| 75-180 µm | % | 80.0% min. | 95.4 |
| thru 75 µm | % | 10.0% max. | 4.6 |

YMC Co., Ltd.

| YMC*GEL SIL 6 nm S-75 µm | |
|---|---|
| Item | Result |
| Average Particle Size: D50 (µm) | 79 |
| Uniformity Coefficient: D40/D90 | 1.51 |
| Average Pore Size (nm) | 6.5 |
| Specific Surface Area (m²/g) | 761 |
| Pore Volume (mL/g) | 1.23 |
| Volatile Matter (%) | 0.3 |
| pH | 5.9 |

EXAMPLES

Example 1

(±)-5-oxo-3-[(trimethylsilyl)oxy]-1-cyclopenten-1-heptanoic acid methyl ester

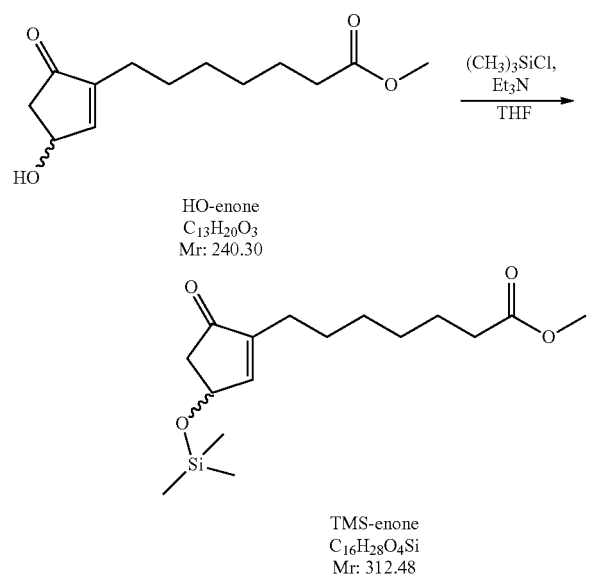

HO-enone
$C_{13}H_{20}O_3$
Mr: 240.30

TMS-enone
$C_{16}H_{28}O_4Si$
Mr: 312.48

1955 g of 3-hydroxy-5-oxo-1-cyclopenten-1-heptanoic acid methyl ester (HO-enone) is dissolved in tetrahydrofuran (20 kg) under inert atmosphere. To the solution 1.7 L of triethylamine and then 1.14 L of trimethylsilyl chloride are added. After reaching the desired conversion the excess of the trimethylsilyl chloride is decomposed with methanol, the reaction mixture is filtered, the precipitate is washed with tetrahydrofuran, to the liquid filtrate triethylamine is added and the mixture is concentrated with evaporation.

The silylated product (TMS-enone) is transferred into the next step without further purification.

Example 2

(±)-(11α,13E)-16-methyl-9-oxo-11,16-bis[(trimethylsilyl)oxy]-13-en-prostanoic acid methyl ester Preparation of the Cuprate Reagent

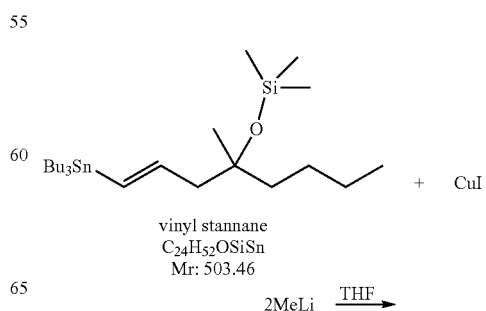

vinyl stannane
$C_{24}H_{52}OSiSn$
Mr: 503.46

-continued

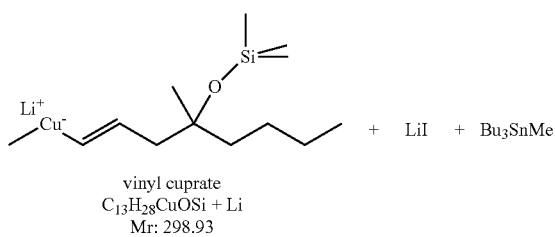

vinyl cuprate
C₁₃H₂₈CuOSi + Li
Mr: 298.93

Decomposition of the Methyllithium Excess

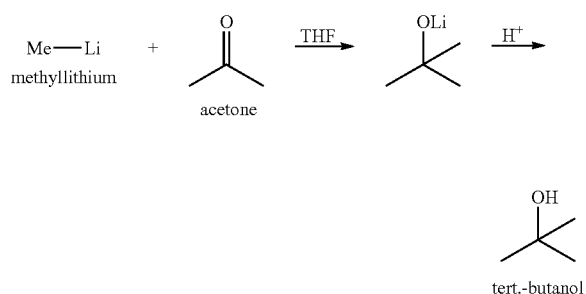

tert.-butanol

Coupling (Conjugated Addition)

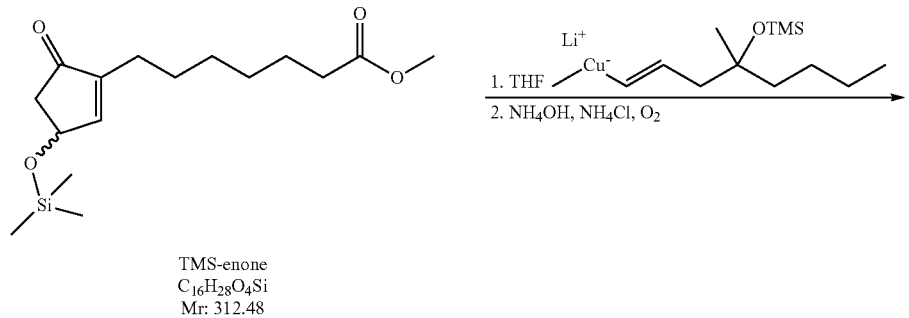

TMS-enone
C₁₆H₂₈O₄Si
Mr: 312.48

Preparation of the Cuprate Reagent 8.4 kg of tributyl[1(E)-4-methyl-4-[trimethylsilyl)oxy]1-octen-1-yl]-stannane (vinyl stannane) is dissolved in tetrahydrofuran in an inert atmosphere. To the solution 2.72 kg of copper(I)iodide is added. The reaction mixture is agitated at room temperature for 30 minutes, then cooled to −35° C. and methyllithium solution equivalent to 34.5 mol of methyllithium is added and the reaction mixture is agitated at −20 to −25° C. If the conversion after 30 minutes of stirring is not sufficient, a further amount of methyllithium solution equivalent to 0.7 mol of methyllithium is added and stirring at −20 −25° C. is continued for another 30 minutes.

Coupling (Conjugated Addition)

The reaction mixture is cooled to −−60° C. and in order to decompose the methyllithium excess, acetone is added. At −55° C. the tetrahydrofuran solution of the TMS-enone derivative is added to the reaction mixture. After 30-40 minutes of agitation the reaction mixture is decomposed by adding it to ammonium chloride-ammonium hydroxide solution (77 kg of water, 9.2 g of ammonium hydroxide solution, 25.3 kg of ammonium chloride).

The decomposed reaction mixture is extracted with methyl tert.-butyl ether, the organic phase is washed with sodium hydrogen sulfate in sodium chloride solution, and then with saturated sodium chloride solution, then dried over sodium sulfate.

The evaporated reaction mixture is transferred into the next reaction step without further purification.

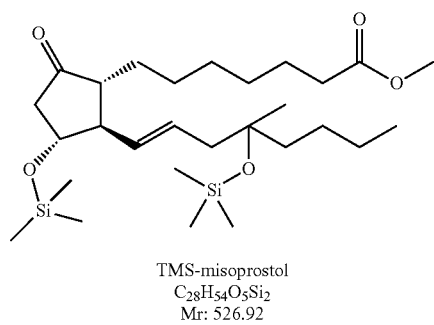

TMS-misoprostol
C₂₈H₅₄O₅Si₂
Mr: 526.92

Example 3

Misoprostol (±)-(11α,13E)-11,16-dihydroxy-16-methyl-9-oxo-13-en-prostanoic acid methyl ester

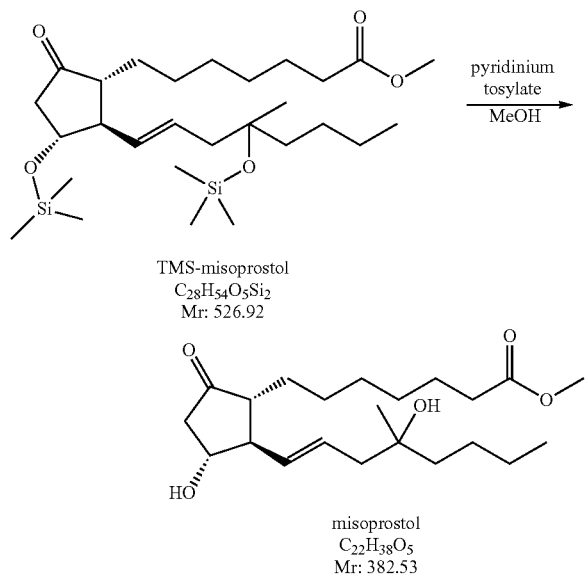

TMS-misoprostol
$C_{28}H_{54}O_5Si_2$
Mr: 526.92 misoprostol
$C_{22}H_{38}O_5$
Mr: 382.53

The TMS-misoprostol (8.11 mol) prepared in the coupling reaction according to Example 2. is dissolved in methanol (17 kg) at room temperature, 205 g of pyridinium tosylate is added to it and the mixture is agitated until the desired conversion is reached. The mixture is then let onto sodium chloride solution. The product is extracted with methyl tert.-butyl ether, the united organic phase is washed with sodium chloride solution, dried over sodium sulfate, filtered and the filtrate solution is evaporated.

Example 4

Misoprostol

The crude misoprostol concentrate (8.11 mol) prepared according to Example 3. is dissolved in diisopropyl ether and purified by chromatography on a column made of 100 kg of silica gel (Kieselgel Si 60 (0.063-0.200 mm)) using as eluent stepwise gradient mixtures of diisopropyl ether:acetone:methanol and 0.05% formic acid, wherein diisopropyl ether:acetone:methanol=100:5:2, 100:10:2, 100:0.5:5, 100:0.5:7.5.

The united main fraction is concentrated. To the diisopropyl ether solution of the main fraction hexane is added until it undergoes opaque, then it is filtered through a 1.6 kg active carbon bed using hexane:acetone=5:1 and hexane:acetone=1:1 solvent mixtures. The filtrate containing the product is concentrated, during concentration the solvent is changed to toluene.

The pre-purified misoprostol concentrate is purified by chromatography using a column of 20 kg of silica gel (Kieselgel Si 60 (0.063-0.200 mm) and eluent mixtures made of dichloromethane:acetone=10:1, 0.05% formic acid, dichloromethane:acetone=7:1, 0.05% formic acid, methyl tert.-butyl ether:acetone=2:1, 0.05% formic acid.

The aim of the filtration chromatography is to remove the contaminations arising from the solvents used during the purification, therefore to this chromatography distilled solvents are used.

The main fraction of the chromatography is neutralized with sodium hydrogen carbonate solution, washed to neutral with water, dried over sodium sulfate which contains active carbon, filtered, evaporated and made solvent-free.

Yield: 1.65 kg, 53% (calculated on HO-enone), colorless oil.

Example 5

Misoprostol

The crude misoprostol concentrate (1.3 mol) prepared from 1.3 mol of enone according to Example 3., is dissolved in methyl tert.-butyl ether and purified by chromatography using a column made of 22.5 kg of silica gel (YMC S75) and eluent mixtures made of diisopropyl ether:isopropanol=15:1, 0.05% formic acid and diisopropyl ether:isopropanol=10:1, 0.05% formic acid.

The united main fraction is washed with sodium hydrogen carbonate solution and then with sodium chloride solution, the neutralized solution is evaporated. The concentrate obtained after evaporation is dissolved in dichloromethane and purified by chromatography using silica gel column (Kieselgel Si 60 (0.063-0.200 mm) and eluent mixtures made of dichloromethane:acetone=10:1, 0.05% formic acid, dichloromethane:acetone=7:1, 0.05% formic acid and methyl tert.-butyl ether:acetone=2:1, 0.05% formic acid.

To the filtration chromatography distilled solvents are used.

The united main fraction is washed to neutral with sodium hydrogen carbonate solution and then with water, dried over sodium sulfate which contains active carbon, filtered and evaporated to solvent-free.

Yield: 275 g, 55% (calculated to HO-enone), colorless oil.

The invention claimed is:

1. A process of preparing compounds of general formula I,

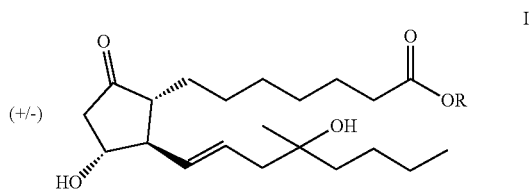

where R represents straight- or branched-chain C1-4 alkyl group, which comprises cuprate coupling of a vinyl cuprate of general formula II

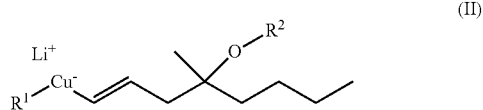

wherein R2 stands for H or an alcohol-protecting group, optionally containing silicon atom or a cyclic or open-chain alkyl group containing oxygen atom; and R1 represents C1-6 alkyl group;

with a protected enone of general formula IV

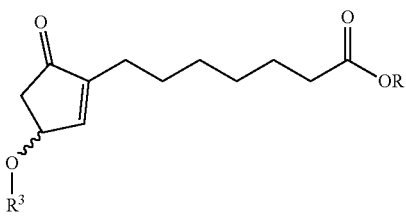

where R3 represents THP- or trialkylsilyl group and R is as defined above to produce a compound of general formula (V)

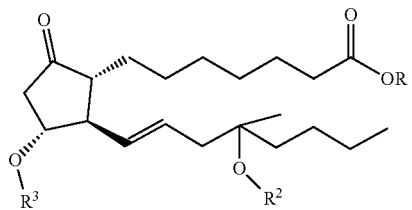

where the meanings of R, R2 and R3 are as defined above,
removing the protecting groups of the compound of general formula (V) and
purifying the compound of general formula (I) by chromatography;
wherein the compound of general formula (II) is prepared by reacting a vinyl stannane of general formula III with copper halide CuX and alkyllithium R1Li

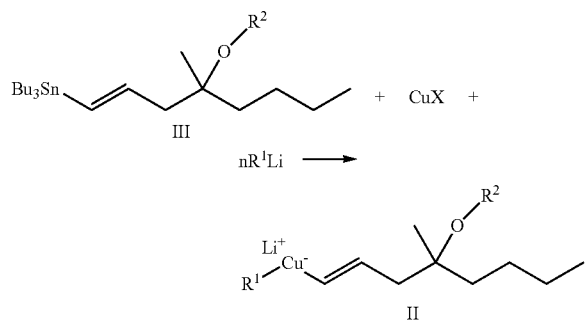

where
X means iodo atom, bromo atom, CN, SCN, OSO2CF3 group,
n>2, if R2 is other than hydrogen atom, and n>3, if R2 is hydrogen atom; and
wherein an excess of the alkyllithium, which is in an amount compared to the Cu(I) iodide
in the case where R2≠H in 2-2.4 molar ratio,
in the case where R2=H in 3-3.4 molar ratio,
is decomposed before the coupling reaction of the compounds of the general formula II and IV.

2. The process of claim 1, wherein the decomposition of the excess alkyllithium is carried out with ketone, ester or trialkylsilyl halogenide compounds.

3. The process of claim 2, wherein the decomposition of the excess alkyllithium is carried out with acetone or ethyl acetate.

4. The process of claim 1, wherein the purification of the compound of general formula (I) comprises purification chromatography and filtration chromatography.

5. The process of claim 4, wherein the purification chromatography removes the technological impurities originating from reagents or side reactions, including related isomeric impurities, and the filtration chromatography removes the contaminations of solvents used as eluent in the purification chromatography.

6. The process of claim 4, wherein the purification is carried out on silica gel column by gravity column chromatography.

7. The process of claim 6, wherein the chromatography on silica gel uses a multicomponent stepwise gradient mixture as eluent.

8. The process of claim 7, wherein the multicomponent mixture contains 0.01-0.1% acid.

9. The process of claim 8, wherein the acid is acetic acid or formic acid.

10. The process of claim 8, wherein eluents of the silica gel chromatography contain 0.05% of formic acid.

11. The process according to claim 4, wherein the purification chromatography uses
(a) spherical silica gel having average particle size of 79 µm; or
(b) irregular silica gel having a size of 0.063-0.200 mm silica gel, then the united main fraction is concentrated and, with adding an apolar solvent, passed through an activated carbon bed.

12. The process of claim 11, where a multicomponent stepwise gradient mixture containing diisopropyl ether, C1-6 alcohol and 0.05% of formic acid and optionally acetone and/or methyl ethyl ketone is used as eluent.

13. The process of claim 11, where the multicomponent stepwise gradient mixture is
in point (a): diisopropyl ether: isopropanol solvent mixture containing 0.05% formic acid,
or
in point (b): diisopropyl ether: acetone: methanol solvent mixture containing 0.05% formic acid.

14. The process according to point (b) of claim 11, wherein hexane:acetone solvent mixtures are used on the activated carbon bed.

15. The process of claim 4, wherein the filtration chromatography is performed with irregular silica gel column having a size of 0.063-0.200 mm and stepwise gradient mixtures of dichloromethane:acetone and methyl tert.-butyl ether:acetone solvents, containing 0.05% formic acid is used as eluent.

16. The process according to claim 12, wherein the fractions from the chromatography are optionally washed to neutral pH.

17. The process of claim 1, wherein the alcohol-protecting group containing silicon atom in the definition of $R^2$ comprises a trimethylsilyl group, a triethylsilyl group or a tert-butyldimethylsilyl group.

18. The process of claim 1, wherein the cyclic or open-chain alkyl group containing oxygen atom in the definition of $R^2$ comprises a tetrahydropyranyl group, a methoxymethyl group or an ethoxymethyl group.

* * * * *